United States Patent [19]

Blackburn et al.

[11] Patent Number: 4,535,636

[45] Date of Patent: Aug. 20, 1985

[54] TENSILE TESTING APPARATUS

[75] Inventors: Linda B. Blackburn; John R. Ellingsworth, both of Hampton, Va.

[73] Assignee: The United States of America as represented by the Administrator of the National Aeronautics and Space Administration, Washington, D.C.

[21] Appl. No.: 590,923

[22] Filed: Mar. 19, 1984

[51] Int. Cl.³ .......................... G01N 3/08; G01N 3/18
[52] U.S. Cl. ........................................ 73/831; 73/856
[58] Field of Search ............... 73/831, 833, 826, 860, 73/856

[56] References Cited

U.S. PATENT DOCUMENTS

| | | | |
|---|---|---|---|
| 1,512,491 | 10/1924 | Scott | 73/792 |
| 1,888,755 | 11/1932 | Barr et al. | 73/826 |
| 2,154,280 | 4/1939 | Nadai et al. | 73/791 |
| 2,436,317 | 2/1948 | Manjoine | 73/782 |
| 2,545,482 | 3/1951 | Manjoine et al. | 73/789 |
| 2,660,881 | 12/1953 | Van Degrift | 73/577 |
| 2,917,920 | 12/1959 | Robinette, Jr. et al. | 73/781 |
| 3,316,757 | 5/1962 | Fletcher et al. | 73/831 |
| 3,482,439 | 12/1969 | Baker | 73/831 |
| 4,114,420 | 9/1978 | Browning | 73/826 |

*Primary Examiner*—Anthony V. Ciarlante
*Attorney, Agent, or Firm*—Howard J. Osborn; John R. Manning; Wallace J. Nelson

[57] ABSTRACT

An improved mechanical extensometer for use with a constant load creep test machine 10, wherein the dead weight of the extensometer is counterbalanced by two pairs of weights 70,90 and 80,100 connected through a pulley system 68, 78, 88 and 98 to rod extension 55,56 and 59,60, leading into the furnace 20 where test sample S is undergoing elevated temperature (above 500° F.) tensile testing. Novel gripper surfaces, conical tip 119 and flat surface 122, are provided in each sample engaging platens 38 and 40 to reduce the grip pressure normally required for attachment of the extensometer to the specimen and reduce initial specimen bending normally associated with foil-gage metal testing.

6 Claims, 7 Drawing Figures

TENSILE TESTING APPARATUS

ORIGIN OF THE INVENTION

The invention described herein was made by employees of the U.S. Government and may be manufactured and used by or for the Government for governmental purposes without the payment of any royalties thereon or therefor.

BACKGROUND OF THE INVENTION

This invention relates to an improved mechanical extensometer employing a displacement transducer for strain measurement of foil-gage metals in elevated (above 500° F.) temperature tensile tests. Although optical techniques and electrical resistance strain gages are also currently accepted methods of strain measurement, each has disadvantages which make them unsuitable for elevated temperature tests on foil-gage metals. Optical techniques require direct readings by a trained operator. Such direct readings are generally subject to operator error, highly labor intensive and not amenable to automated data collection systems. Electrical resistance strain gages are commonly restricted to use at temperatures below 500° F. Strain gages for use above 500° F. are available, but are costly and difficult to attach properly. Also, it has been found that attachment of strain gages to foil-gage metals affects the mechanical behavior of the material. Mechanical extensometers offer the advantages of being capable of operation at temperatures in excess of 500° F., ready availability, relatively inexpensive and easily incorporated into test setups using automated data collection systems. Application of mechanical extensometers to foil-gage metals, however, poses several concerns. In certain tensile tests, the additional weight of the extensometer on the specimen may greatly exceed the allowable one percent of the maximum test load. Also, the grip pressure required for attachment of the extensometer to the specimens may induce bending stresses in foil-gage materials.

There is therefore a definite need in the art for an improved mechanical extensometer for testing foil-gage metals.

Accordingly, it is an object of the present invention to provide a new and improved mechanical extensometer for strain measurement of foil-gage materials in elevated temperature tensile tests.

Another object of the present invention is an apparatus for reducing the grip pressure requirement for foil-gage materials in a mechanical extensometer.

Another object of the present invention is an apparatus for alleviating the weight contribution of a mechanical extensometer during tensile testing of elevated temperature foil-gage material specimens.

A further object of the present invention is an improved grip insert mechanism for mechanical extensometers that reduce error in tensile testing of foil-gage materials.

An additional object of the present invention is a novel counterweight arrangement for reducing the weight stress on foil-gage test specimens during tensile testing thereof.

The foregoing and additional objects of the present invention are attained by providing a pair of vertically extending connecting rods attached to each of the top and bottom furnace platens of an extensometer and slidably extending these rods through the top of the furnace wall. Individual ceramic insulators are secured to each of the rod ends that extend through the furnace wall. Tapped holes are provided approximately 180° apart through the conventional top furnace platen of the extensometer for threaded receipt of one pair of the rods. The bottom furnace platen is provided with integrally secured extensions and is also provided with a pair of 180° spaced tapped openings therethrough for threadingly receiving the other pair of connecting rods. The connecting rods are thus disposed such that the rods are essentially positioned at right angles to each other. The four ceramic insulators are connected by flexible wire, through a pulley system, to four weights. Each pair of weights is designed to offset the weight contribution of one-half the weight applied by the mechanical extensometer. The pulley system is suspended from a main support block integrally attached to a back support plate that, in turn, is fixed to the tensile test frame. The main support block is provided with vertically adjustable mechanisms to permit correct positioning of the connecting rods extending through the furnace top.

Novel grip inserts are provided on the top and bottom furnace platens to further reduce the grip pressure required for attachment of the specimen and to reduce bending stresses induced in the foil-gage test specimen as a result of extensometer attachment. These inserts are secured to the adjustable faces of each platen through which the test specimen is positioned. One insert in each platen is provided with a flat edge surface and the facing insert is a precision conical tip.

BRIEF DESCRIPTION OF THE DRAWINGS

A more complete appreciation of the invention and many of the attendant advantages there of will be more readily apparent as the same becomes better understood by reference to the following detailed description when considered in connection with the accompanying drawings wherein.

DETAILED DESCRIPTION OF THE INVENTION

Figure 1:
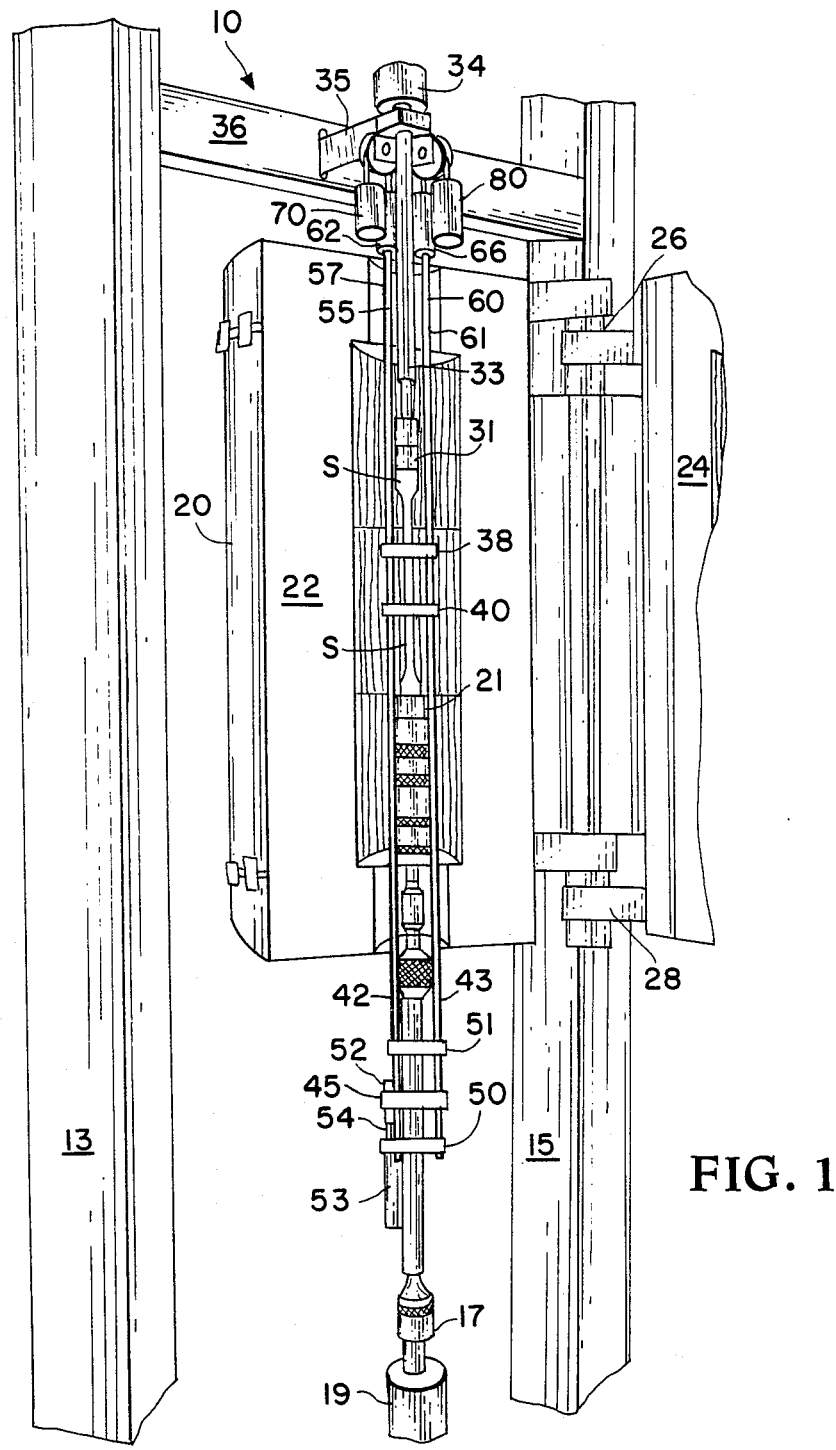
FIG. 1 is a part perspective view of the improved extensometer according to the present invention with parts thereof omitted for clarity.

Referring now to the drawings, the improved tensile test apparatus of the present invention is partially shown and designated generally by the reference numeral 10. Apparatus 10 is supported by a base and a top frame (not shown) connected to vertical frame bars 13 and 15. A vertically extending bottom shaft 17 is disposed essentially intermediate vertical frame bars 13 and 15 and is rigidly secured to housing 19 leading to the base of apparatus 10. Shaft 17 terminates within furnace 20 at sample retaining chuck 21 for securing one end of test specimen S. Furnace 20 is a conventional clam-shell type furnace and is supported by vertical frame bar 15 at the hinge line thereof and includes furnace halves 22 and 24 (partially shown) connected at hinges 26 and 28.

The other end of test specimen S is retained by chuck 31 also disposed within furnace 20. Chuck 31 forms the terminus of vertically depending shaft 33 extending through the top of furnace 20 with the other end thereof being connected to a worm gear drive 34 leading from a conventional drive motor therefor (not shown) and also affixed to vertical frame bars 13 and 15. Shaft 33 also extends through a pulley bracket assembly 35 vertically adjustable affixed to a horizontal beam 36 integrally connected to vertical frame bars 13 and 15 above and spaced from furnace 20. The details of the pulley bracket 35 assembly and its connected structure will be more fully described hereinafter.

The test section of test specimen S constitutes an intermediate length thereof and is secured between an upper and lower furnace platen disposed within furnace 20 and designated, respectively, by reference numerals 38 and 40.

Figure 3:
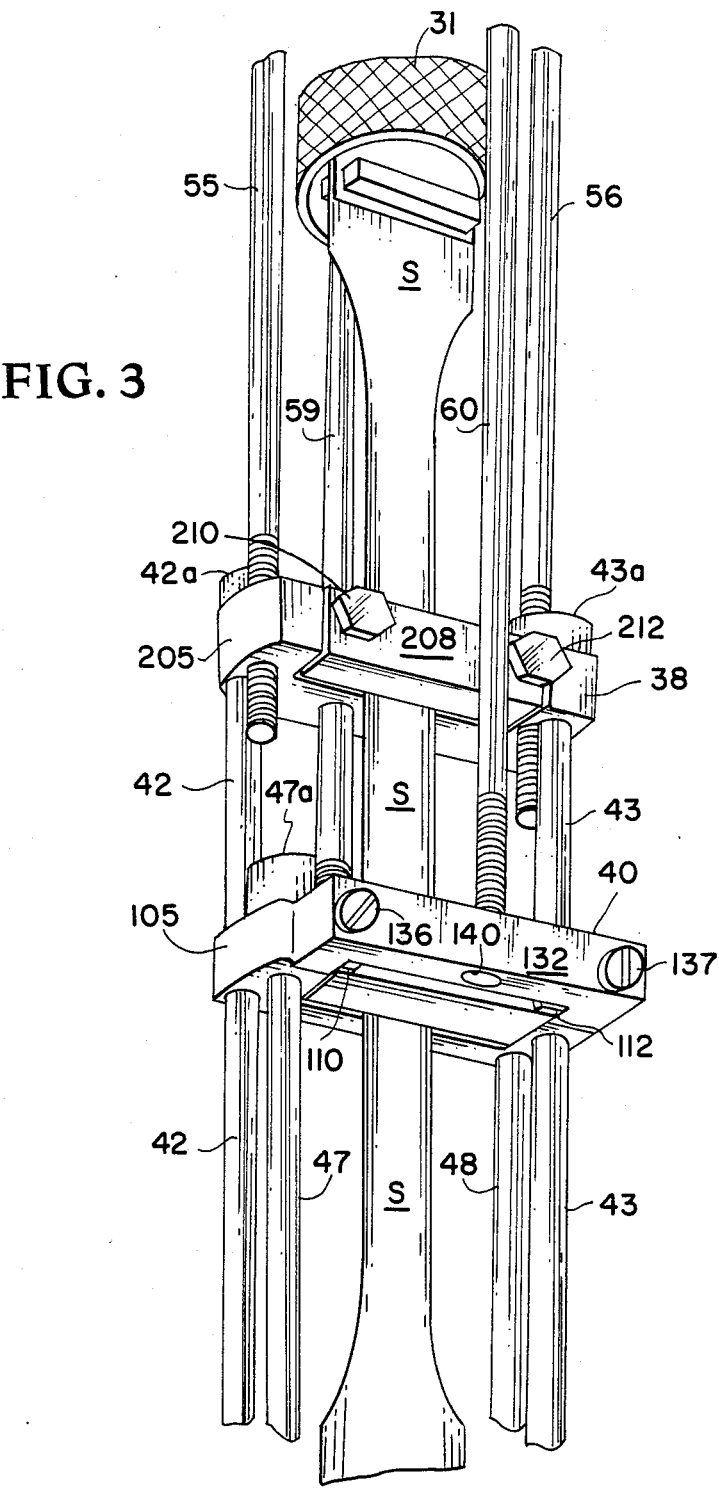
FIG. 3 is an enlarged view of the test section of the extensometer shown in FIG. 1.

As shown more particularly in FIG. 3, a pair of depending rod elements 42,43 (having integrally secured heads 42a, 43a) slidably extend through upper furnace platen 38 and lower furnace platen 40 for fixed attachment with a first U-shaped platen 45 (FIG. 1) that is slidably disposed about vertical shaft 17.

A pair of similar rod elements 47,48 having respective integrally secured heads 47a (and one not visible in the drawing), slidably extend through lower furnace platen 40 and first U-shaped platen 45 (FIG. 1) and are fixedly attached to a second U-shaped platen 50. Thus, any vertical movement of upper furnace platen 38 causes a corresponding and identical movement of first U-shaped platen 45 while any vertical movement of lower furnace platen 40 causes a corresponding and identical movement of second U-shaped platen 50. A guide 51 is secured to rods 42, 43 and slidably disposed about shaft 17 to maintain alignment of the extensometer about vertical shaft 17. A linear variable displacement transducer (LVDT) 53 is attached to U-shaped platen 50 and an adjustable micrometer 52 is attached to platen 45 for measuring relative linear separation thereof during tensile testing of sample S as an indication of actual strain on the sample. LVDT 53 is provided with a push rod 54 that extends through U-shaped platen for contact with the tip of micrometer 52. LVDT is also connected to an automated data acquisition system (not shown) for displaying and recording sample displacement data during extensometer testing thereof.

Figures 2, 2A:
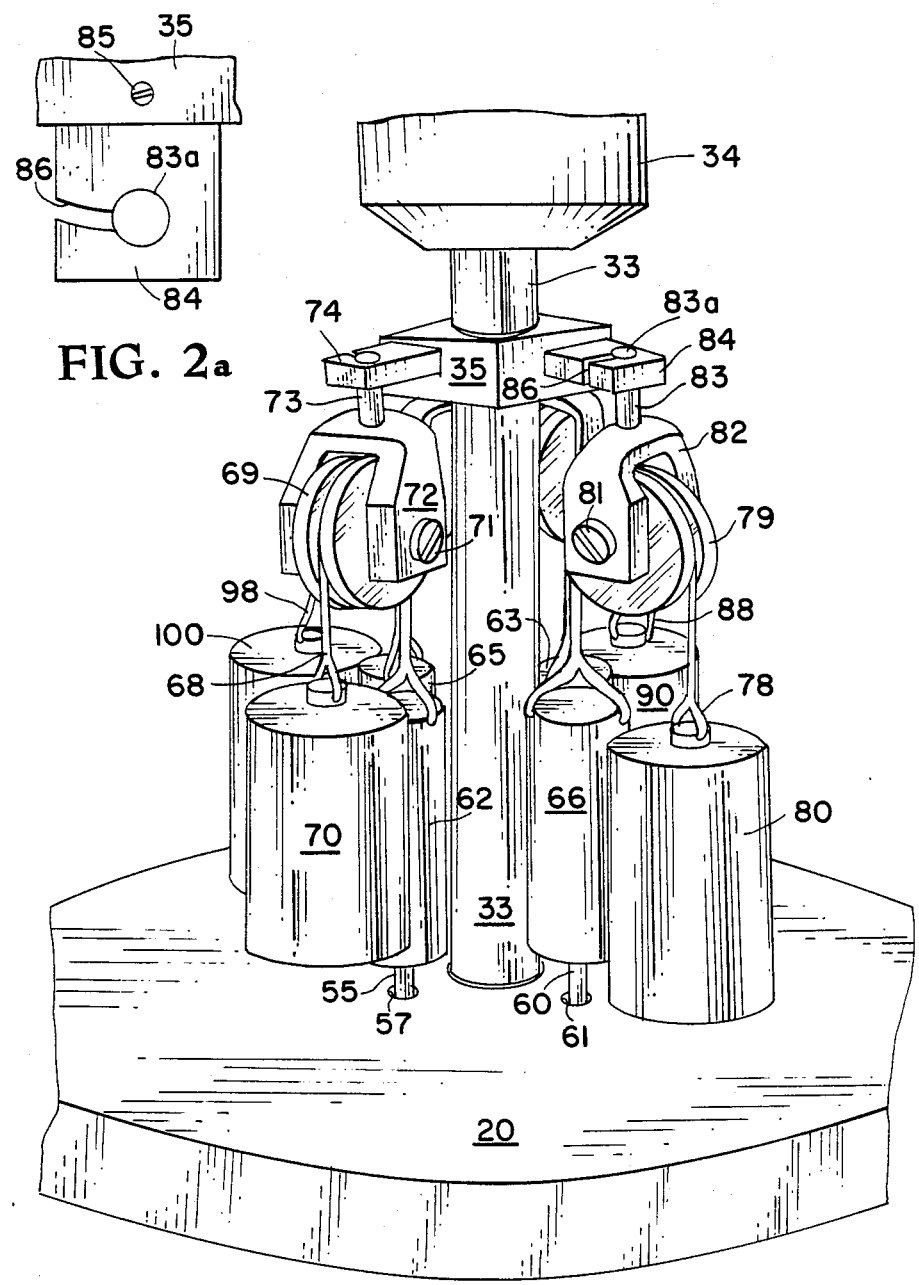
FIG. 2 is an enlarged view of the counterweight system for the extensometer as shown in FIG. 1.
FIG. 2a is a partial top view of a portion of the system shown in FIG. 2.

Upper furnace platen 38 threadingly receives a first pair of vertically extending rod elements 55, 56 leading through an opening 57 (and one not shown) in the top of furnace 20. A second similar pair of rod elements 59,60 are threadingly connected to integral structure on bottom furnace platen 40 and also vertically extend through an opening 61 (and one not shown) in the top of furnace 20. The ends of rod elements 55,56 extending through the top of furnace 20 are threadingly or otherwise conventionally attached to respective ceramic insulators 62,63 as more clearly illustrated in FIG. 2. Similarly, the end of rod elements 59,60 extending through furnace 20 are provided, respectively, with ceramic insulators 65,66. A flexible support wire or cable 68 secured to ceramic insulator 62 extends over a rotatable pulley 69 and is connected at its other end to a counterweight 70. Pulley 69 is rotatable about axle 71 extending through U-bracket 72, that is rotatable suspended via arm 73 from extension 74 on pulley bracket assembly 35. Similarly, a flexible support wire or cable 78 is secured to ceramic insulator 66 and extends over rotatable pulley 79 to connect with weight 80. Pulley 79 is rotatable about axle 81 extending through U-bracket 82 that is rotatable suspended via arm 83 from extension 84 on pulley bracket assembly 35. Ceramic insulators 63 and 65 are connected to respective weights 90,100 via respective cables or wires 88,98 in similar fashion and need not be further explained in the interest of brevity.

Figure 4:
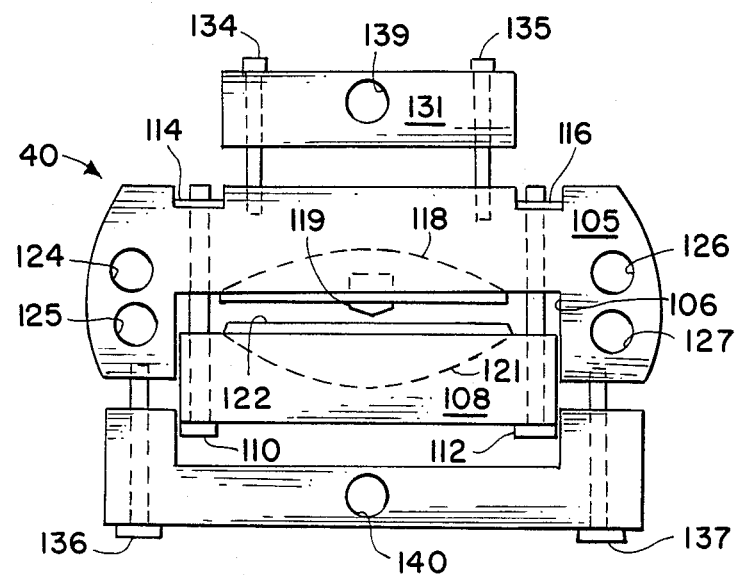
FIG. 4 is a top view of the lower sample holding platen used in the extensometer shown in FIG. 1.
Figure 5:
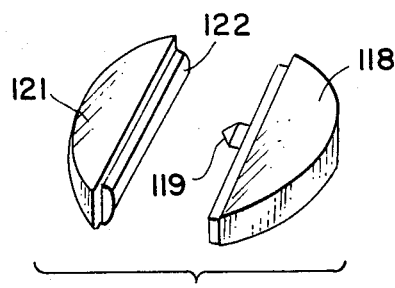
FIG. 5 is a view of the test specimen grip surface inserts employed in the platen shown in FIG. 4.
Figure 6:
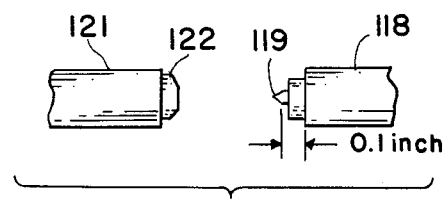
FIG. 6 is a side view of the test specimen grip inserts shown in FIG. 5.

Referring now more particularly to FIGS. 4–6, the details of lower furnace platen and the sample gripping platen inserts will now be described. As shown in the top view thereof (FIG. 4), lower furnace platen 40 includes a first plate 105 having an elongated central recessed or cutaway area 106 formed along a substantial length thereof. An elongated second plate 108 is slidably received by plate 105 in recessed area 106. A pair of hex-headed bolts 110, 112 pass through suitable openings in plates 105 and 108 for connection thereof. Tapped nuts 114,116 are provided in mating recesses formed in plate 105 for respective retention of bolts 110 and 112. A gripper insert 118 having a precision machined conical tip 119 formed thereon is secured within plate 105. A second gripper insert 121 having a flat edge surface 122 formed thereon is secured within plate 108. Flat edge surface 122 and conical tip 119 face each other and serve to contact and secure sample S therebetween when bolts 110 and 112 are tightened to move plates 108 and 105 toward each other. The ends of plate 105 are each provided with a pair of openings therethrough as designated by reference numerals 124,125 and 126,127. As described hereinbefore in reference to FIG. 3, openings 124 and 127 are slightly larger than openings 125 and 126 and serve to slidably receive rods 42 and 43 therethrough, and openings 125 and 126 receive depending rods 47,48. A pair of side extensions 131,132 are bolted to plate 105 via respective bolt pairs 134,135 and 136,137. Side extension 131 is provided with tapped opening 139 for receiving upwardly extending rod 59. Side extension 132 is provided with a tapped opening 140 for receiving upwardly extending rod 60 as described hereinbefore.

Upper furnace platen 38 is of similar construction to lower furnace plate 40, but omits the side extension plates therefrom. Thus, referring back to FIG. 3, upper furnace platen 38 would include plate and adjusting bolts 210 and 212 serving to connect the plates 205,208 and retain sample specimen S therebetween via identical conical and flat plate gripper inserts, not shown. Plate 205 also is provided with tapped end openings therein (not designated) for vertically extending rod pair 55,56, and smooth openings (also not designated) for rod pair 42,43.

OPERATION

The operation of the invention is now believed apparent. A foil-gage metal specimen S is secured to chucks 21,31 in a conventional manner. In a specific test the specimens were fabricated from nominal 0.003 inch thick foil and 0.049 inch thick sheet using annealed titanium alloy Ti-6Al-4V. The samples were 8.00 inch long, 0.75 inch wide at the 2.00 inch long end portions and $0.500 \pm 0.010$ inch wide at the remaining center test section. Titanium doublers were spot welded to both sides of each end of the foil-gage specimen to prevent localized yielding, during testing, by the bearing loads induced by the end alignment pins passing therethrough. All creep tests were conducted in a constant load creep test machine 10 equipped with a clam-shell furnace 20. In the illustrated embodiment, chuck 21 was fixed and only chuck 31 had load applied thereto. The creep test machine could also be adapted for chuck 31 to be fixed and load applied to chuck 21 alone, if the test so dictated. Uniform temperature over the specimen length was achieved in furnace 20 by an automated, zone-control temperature and power controller, not illustrated herein in the interest of clarity. Specimen load was measured with a "mini" load cell positioned in the lower portion of the load train beneath furnace 20. Strain measurements were made using an Applied Test Systems, Inc. Series 4100/4200 Metals Testing extensometer with LVDT 53. The counter-balance system of the present invention was attached to the extensometer and reduced the axial load imposed thereby to less than one percent of the total maximum test load. Also, the counter-balance system and the novel grip insert faces 119 and 122 employed in platens 38 and 40 reduced the grip pressure normally required for attachment of the extensometer to the specimen and thereby reduced the amount of initial specimen bending normally associated with extensometer testing of this type. Each pair of weights served to counter-balance one-half of the dead weight applied to the foil-gage specimen when attaching the mechanical extensometer through the four connecting rods 55,56; attached to top furnace platen 38 and 59,60 attached to bottom furnace platen 40. Each weight pair 70,90 and 80,100, is calibrated to equal one-fourth of the weight of the attached extensometer structure; i.e., the sum of the weight for the ceramic insulators 62, 63, 65 and 66, attached rods 55, 56, 59 and 60, platens 38, 40, rods 42, 43, and 47, 48, U-shaped platens 45, 50 and LVDT 53. The weight of all these attached components is thus counterbalanced by paired counter-weights 70, 90, and 80, 100 and sample specimen S is creep tested without the mechanical extensometer detectably influencing or interfering with the test. Pulley bracket assembly 35 is vertically adjusted to ensure that adequate clearance is maintained between the individual weights and the top of furnace 20. That is, the threaded ceramic insulators are rotatably adjusted on their respective connected rods to ensure each of the weights and ceramic rod ends will remain spaced from and not come in contact with furnace top 20 during a test. As shown more particularly in FIG. 2a, extension 84 on pulley assembly bracket 35 and the other corresponding extensions, can be adjusted in length through set screw 85 to ensure proper positioning of rods 55, 56, 69 and 60 as they extend through furnace top 20 and prevent the rods from rubbing against the drilled hole in furnace top 20. Also, the ability of the pulley to rotate, e.g., 72 to rotate at 73, and for arm 84 and its attached head 84a to freely move within arcuate slot 86 in extension 84, reduces torsional stresses that might develop with rigid systems. In the interest of brevity only one extension 84 has been described in detail, but it is to be understood that extensions 74 and the other two not illustrated are of identical construction. During creep testing test specimen S is stretched by the force exerted on chuck 31 and the test area connected between furnace platens 38 and 40 will be expanded or stretched. Due to the positive connection of platens 38, 40 with U-shaped platens 45 and 50, an equal separation of these platens will occur and this linear displacement or distance is directly measured by LVDT 53. A Hewlett-Packard (HP) Data Acquisition System (DAS) was employed in connection with the LVDT to indicate and record the strain measurement for the foil-gage specimens. This system included an HP9845A Desktop Computer, an HP3455A Digital Voltmeter, an HP3495A Scanner and an HP98035A Real Time Clock which monitored and recorded specimen load, temperature, strain, power supply voltage for the load cell and extensometer transducer and elapsed time.

At 800° F. and 45 ksi, the foil-gage test specimens exhibited approximately four times higher creep rate than the sheet sample in the steady state portion. At 1000° F. and 25 ksi the 0.003 inch foil specimen again exhibited the higher creep rate but the steady state rate was only twice as great as the 0.049 inch sheet specimen at this temperature stress combination.

It is thus seen that the counter-balance extensometer of the present invention is a valuable tool in conducting measurements of actual strain on foil-gage materials. This system significantly increases the speed and accuracy of basic strain analysis for foil-gage materials and should prove a valuable research tool in this area.

Although the invention has been described relative to a specific embodiment thereof, it is not so limited and numerous variations and modifications of the invention will be readily apparent to those skilled in the art without departing from the spirit and scope of the invention. For example, although the specific test specimens described herein are foil-gage metal, this invention may be employed for mechanical extensometer testing of any weak material where the weight of the extensometer represents a sizable fraction of the yield force. Thus, the use of this invention for composite, polymeric and explosive formulations at room and elevated temperatures is considered within the scope thereof and should prove beneficial to automotive, power generation, defense and aerospace industries as well as in basic research and development. It is therefore to be understood that within the scope of the appended claims that the invention may be practiced otherwise than as specifically described herein.

What is claimed as new and desired to be secured by Letters Patent of the United States is:

1. In combination with an extensometer for accurately measuring strain on foil-gage type materials under elevated temperature test conditions including a displacement transducer strain measuring device, a clam shell type furnace, a pair of platens for supporting a test specimen within the furnace, and means for exerting a constant tensile load on the test sample supported therein, the improvement therewith comprising:
    counterbalance means connected to each of said pair of platens to offset the weight contribution of the extensometer on the test specimen,
    sample engaging means forming part of each of said pair of platens, said sample engaging means in each said platen comprising a first flat edge surface and a second conical tip surface,
    said flat edge surface and said conical tip surface engaging and retaining a foil-gage type test specimen therebetween, and
    means for adjusting relative movement of said flat edge surface and said conical tip surface to adjust and maintain the engagement thereof with the test specimen.

2. The extensometer of claim 1 wherein said counterbalance means includes a first pair of connecting rods secured to and extending vertically from one of said platens,
  a second pair of connecting rods secured to and extending vertically from the other of said pair of platens,
  each member of said first and said second pair of connecting rods being disposed approximately 90° from the adjacent rod and approximately 180° from the other member of the pair,
  each member of said first and said second pair of connecting rods snugly and slidably extending through the top of the furnace, and
  ceramic insulators connected to and forming extensions to each of said connecting rods.

3. The extensometer of claim 2 wherein said counterbalance means further includes:
  individual counterweights attached to each of said ceramic insulators,
  a fixed support bar disposed vertically spaced from and adjacent to said ceramic insulators,
  four individual pulleys disposed in 90° relationship and suspensed for rotative movement from said fixed support bar,
  cable means for each said ceramic insulator connected at one end thereof to one of said insulators,
  each said cable means extending from its connected one of said insulators around one of said pulleys and having the other end thereof connected to a counterweight to thereby provide a pair of counterweights for each said pair of connecting rods whereby, each pair of counterweights serve to offset the weight contribution of one-half of the mechanical extensometer.

4. An improved extensometer for accurately measuring strain on foil-gage materials under elevated temperature test conditions comprising in combination with a constant creep load test machine and a clam-shell type furnace,
  sample engaging chucks for retaining a foil-gage test sample within the test machine and having load applying means connected thereto for applying a constant tensile load on the sample,
  an extensometer secured to the test section of the test sample within the furnace,
  said extensometer including a first pair of spaced platens attached to the test section of the test sample,
  said first pair of spaced furnace platens being individually and positively connected to a second pair of spaced platens disposed exteriorly of the furnace such that any linear relative movement of said first pair of spaced platens will be transferred to an identical relative linear movement of said second pair of spaced platens,
  means attached to and measuring linear displacement of said second pair of spaced platens as a function of strain on the test sample attached to said first pair of spaced platens, and
  weight means connected to said first pair of platens to counterbalance the combined weight of the extensometer acting on the test sample.

5. The improved extensometer combination of claim 4 wherein:
  said first pair of spaced platens includes test sample engaging means forming part of each member of said platen,
  said sample engaging means, in each said platen comprising,
  a first flat edge surface and a second conical tip surface,
  said flat edge surface and said conical tip surface engaging and frictionally retaining a foil-gage test specimen therebetween, and
  means for adjusting relative movement of said flat edge surface and said conical tip surface to adjust and maintain the engagement thereof with the test specimen.

6. The improved extensometer combination of claim 4 wherein:
  each of said pair of first spaced platens have a pair of connected rod members vertically extending therefrom and passing through the top of the furnace,
  a ceramic insulator terminus secured to each said rod member exterior of the furnace top,
  a cable or wire connected to each said ceramic insulator and extending over a suspended pulley and connected to a weight, and
  each weight serving to counterbalance one-fourth of the dead weight of the extensometer applied to the test sample.

* * * * *